(12) United States Patent
Dapper et al.

(10) Patent No.: US 8,437,858 B2
(45) Date of Patent: May 7, 2013

(54) VISUAL PROSTHESIS SYSTEM FOR DISPLAYING VIDEO IMAGE AND TEXT DATA

(75) Inventors: Marcus Dapper, Bonn (DE); Christian Martin Kopka, Bonn (DE)

(73) Assignee: IMI Intelligent Medical Implants, AG, Zug (CH)

( * ) Notice: Subject to any disclaimer, the term of this patent is extended or adjusted under 35 U.S.C. 154(b) by 124 days.

(21) Appl. No.: 12/921,714

(22) PCT Filed: Mar. 18, 2008

(86) PCT No.: PCT/EP2008/002161
§ 371 (c)(1),
(2), (4) Date: Sep. 23, 2010

(87) PCT Pub. No.: WO2009/115097
PCT Pub. Date: Sep. 24, 2009

(65) Prior Publication Data
US 2011/0004271 A1     Jan. 6, 2011

(51) Int. Cl.
*A61N 1/00* (2006.01)
(52) U.S. Cl.
USPC .......................................................... 607/53
(58) Field of Classification Search ............. 607/53, 607/54
See application file for complete search history.

(56) References Cited

U.S. PATENT DOCUMENTS

| | | | |
|---|---|---|---|
| 6,400,989 B1 | 6/2002 | Eckmiller | |
| 7,003,355 B1 | 2/2006 | Suaning | |
| 2002/0010496 A1 | 1/2002 | Greenberg | |
| 2002/0050518 A1 | 5/2002 | Roustaei | |
| 2004/0117011 A1 | 6/2004 | Aharoni et al. | |
| 2004/0172098 A1 | 9/2004 | Greenberg | |
| 2011/0242617 A1 * | 10/2011 | King et al. | 358/474 |

FOREIGN PATENT DOCUMENTS

| | | |
|---|---|---|
| EP | 1790379 | 5/2007 |
| JP | 2002-278670 | 9/2002 |
| JP | 2007-190064 | 8/2007 |
| WO | WO98/36795 | 8/1998 |
| WO | WO2004/054469 | 7/2004 |
| WO | 2007/006376 | 1/2007 |
| WO | 2008/074478 | 6/2008 |

* cited by examiner

*Primary Examiner* — Scott Getzow
(74) *Attorney, Agent, or Firm* — Workman Nydegger

(57) ABSTRACT

A visual prosthesis system comprises a retina implant at least partly located in the interior of a patient's eye. The retina implant comprises an array of micro-contacts adapted for contacting ganglia of the patient's retinal tissue. The visual prosthesis system further comprises a data processing unit with an additional interface for receiving an external signal from an external signal source, the data processing unit being adapted for converting the external signal into corresponding stimulation data for the retina implant, and a wireless transmission unit adapted for transmitting the stimulation data to the retina implant via wireless transmission. The retina implant is adapted for receiving the stimulation data and for stimulating the micro-contacts according to the stimulation data.

20 Claims, 5 Drawing Sheets

VISUAL PROSTHESIS SYSTEM FOR DISPLAYING VIDEO IMAGE AND TEXT DATA

CROSS-REFERENCE TO RELATED APPLICATIONS

This application is a U.S. Nationalization of PCT International Application No. PCT/EP2008/002161 filed Mar. 18, 2008, entitled "VISUAL PROSTHESIS SYSTEM FOR DISPLAYING VIDEO IMAGE AND TEXT DATA," which is incorporated herein by reference in its entirety.

The invention relates to a visual prosthesis system, to a method for displaying an external signal in a visual prosthesis system, and to a method for displaying text data in a visual prosthesis system.

There exist a variety of different diseases of the retina that are caused by a degeneration of the photosensitive cells of the retina. Examples of degenerative diseases are retinitis pigmentosa, macula degeneration or Usher syndrome. As a result of these degenerative diseases, people slowly loose their vision and eventually suffer from complete blindness. A visual prosthesis system comprising a retina implant is a helpful tool for at least partially re-establishing a modest visual perception and a sense of orientation for blind and visually impaired users. However, it is still difficult to display text, images and video signals on a retina implant in a way that is comfortable for the patient.

It is an object of the patient invention to improve the display of text, image and video data on a retina implant.

The object of the invention is solved by a visual prosthesis system comprising a retina implant at least partly located in the interior of a patient's eye, with the retina implant comprising an array of micro-contacts adapted for contacting ganglia of the patient's retinal tissue. The visual prosthesis system further comprises a data processing unit with an additional interface for receiving an external signal from an external signal source, the data processing unit being adapted for converting the external signal into corresponding stimulation data for the retina implant, and a wireless transmission unit adapted for transmitting the stimulation data to the retina implant via wireless transmission. The retina implant is adapted for receiving the stimulation data and for stimulating the micro-contacts according to the stimulation data.

According to embodiments of the present invention, the data processing unit of the visual prosthesis system is adapted for directly receiving an input signal from an external signal source, for example from a TV set, a DVD player, or a laptop. The external signal is converted into corresponding stimulation data for the retinal implant. The stimulation data is transmitted to the retina implant, and the retinal tissue is stimulated in accordance with the external signal. By directly connecting the external signal source with the data processing unit of the visual prosthesis system, a high quality input signal is used as a starting point for generating stimulation data for the retina implant. For example, text, image and video signals can be provided directly from the external signal source to the data processing unit and may be converted into stimulation data without any degradation of signal quality. For each type of external signals, the most suitable conversion into stimulation data for the retina implant may be chosen. Furthermore, for displaying the respective signal of the external signal source, the full display size provided by the retina implant can be used.

According to a preferred embodiment, the visual prosthesis system further comprises an intrasystem video camera adapted for acquiring a video signal that corresponds to the patient's field of view. The data processing unit is adapted for receiving the video signal from the intrasystem video camera and for converting the video signal into corresponding stimulation data for the retina implant.

In the context of the present application, the term "external signal source" shall comprise any network or device capable of providing an external signal like for example a video signal, an image signal, text data or any other kind of signal to the data processing unit. The intrasystem video camera of the visual prosthesis system is not included by the term "external signal source".

According to a preferred embodiment, the visual prosthesis system comprises input means for selecting either the video signal of the intrasystem video camera or the external signal of the external signal source to be displayed to the patient on the retina implant. The patient may either view the video signal acquired by the intrasystem video camera or an external signal provided by the external signal source. In particular, the patient may toggle between the video signal and the external signal.

For example, the external signal source may be one of: a TV set, a video device, a personal computer, a laptop, a satellite receiver, a DVB receiver, a DVD player.

According to a preferred embodiment, the external signal is one of a video signal, an image signal and text data. For example, the patient may watch TV, movies, video clips, photographs supplied by the external signal source. Furthermore, the patient may access internet pages, read text documents provided by a text processing system, read emails, etc.

According to embodiments of the invention, a visual prosthesis system comprises a retina implant at least partly located in the interior of a patient's eye, with the retina implant comprising an array of micro-contacts adapted for contacting ganglia of the patient's retinal tissue. The visual prosthesis system further comprises an intrasystem video camera adapted for acquiring a video signal, a data processing unit adapted for receiving the video signal from the intrasystem video camera and for converting the video signal into corresponding stimulation data for the retina implant; and a wireless transmission unit adapted for transmitting the stimulation data to the retina implant via wireless transmission. The retina implant is adapted for receiving the stimulation data and for stimulating the micro-contacts according to the stimulation data. The data processing unit is adapted for determining if a received signal comprises text, and for converting the text into corresponding stimulation data for the retina implant according to a dedicated text display mode, wherein the stimulation data is adapted to provide for an optimized legibility of the text by the patient.

For a blind or visually impaired person, being able to read is a very important issue. By providing a dedicated text display mode, the patient may read books, newspapers, e-mails, internet pages, etc. Furthermore, the dedicated text display mode may enable the patient to do computer work.

For reading a particular document, an intrasystem video camera of the visual prosthesis system may acquire a video image of the document, which is displayed on the retina implant. However, text will appear too small, and the patient may not be able to read the text. Therefore, it is proposed to provide a dedicated text display mode. In the text display mode, any kind of received text is displayed in an enhanced manner, to provide for improved legibility. For example, fonts that match with the resolution provided by the retina implant may be employed for displaying the text on the retinal implant. Furthermore, substantially the full display area provided by the retina implant may e.g. be used for displaying the characters of the text. Further preferably, characters of the text may e.g. be scrolled across a display area of the retinal implant.

According to a preferred embodiment, the data processing unit comprises an additional interface for receiving an external signal, the data processing unit being adapted for determining if the external signal comprises text, and for converting the text into corresponding stimulation data for the retina implant according to the dedicated text display mode. Hence, the dedicated text display mode may also be applied to an external signal received via an additional interface of the data processing unit.

In a further preferred embodiment, the text is received via the additional interface as text data, the text data comprising a sequence of character codes. For example, text data may be received from a personal computer or a laptop, in particular from a text processing program, from an internet browser or from an email reader. Displaying text data received from an external source in a dedicated text display mode may enable the patient to interact with his or her personal computer.

According to a further preferred embodiment, the data processing unit comprises a character recognition unit adapted for recognizing characters in a bitmap image, and for converting the bitmap image into text data. The bitmap image may either be provided by the intrasystem video camera or by an external signal source. For example, the bitmap image may be generated by a handheld scanner. The character recognition unit performs pattern recognition in order to determine the characters contained in the bitmap data. The text data determined by the character recognition unit may then be displayed to the patient according to the dedicated text display mode.

For a better understanding of the present invention and to show how the same be carried into effect, reference will now be made by a way of example to the accompanying drawings in which:

FIG. 1 gives an overview of a visual prosthesis system;

Figure 1:
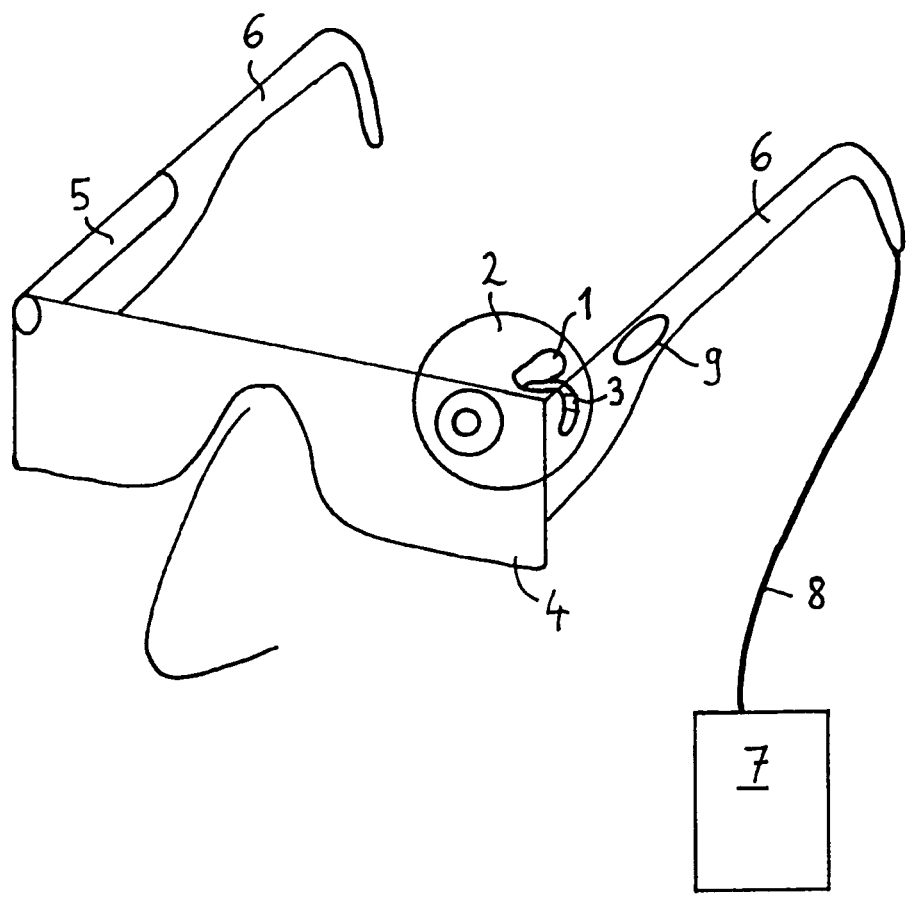

FIG. 1 shows a visual prosthesis system for at least partially reestablishing a modest visual perception and a sense of orientation for blind and visually impaired users. There exist a variety of different diseases of the retina that are caused by a degeneration of the photosensitive cells of the retina. Examples for degenerative diseases are retinitis pigmentosa, macula degeneration or Usher syndrome. As a result of these regenerative diseases, people slowly loose their vision and eventually suffer from complete blindness.

The visual prosthesis system shown in FIG. 1 comprises a retinal implant 1 that may for example comprise an intraocular part located within the eyeball 2 and an extraocular part located at the outer surface of the eyeball 2. The intraocular part of the retinal implant 1 comprises an array 3 of microcontacts that is in direct contact with the patient's retina, wherein the microcontacts are adapted for electrically contacting the retinal tissue.

The visual prosthesis system further comprises a visual interface 4, which may for example be realized as an eyeglass frame. The visual interface 4 comprises a video camera 5, which may be integrated in one of the temples 6 of the eyeglass frame. The visual prosthesis system further comprises a pocket computer 7 that is connected to the visual interface 4 via a wired or wireless connection 8. Video signals acquired by the video camera 5 are transmitted to the pocket computer 7. There, the video signals are transformed into corresponding stimulation data for the array 3 of microcontacts. The stimulation data determined by the pocket computer 7 is provided via the connection 8 to the visual interface 4. There, the stimulation data is transmitted to the retina implant 1 via wireless transmission. For example, a modulated RF signal carrying the stimulation data may be transmitted from a transmission coil 9 to a corresponding receiver coil of the retinal implant 1. The transmission coil 9 may e.g. be integrated into one of the temples 6 of the eyeglass frame. Alternatively, a beam of modulated light, preferably modulated infrared light carrying the stimulation data may be transmitted from the visual interface 4 to the retina implant 1.

At the retinal implant 1, the modulated IR signal or the modulated RF signal is received and decoded. In accordance with the stimulation data, stimulation pulses are applied to the microcontacts of the array 3. The power required for the retinal implant's operation may be supplied by transmitting RF energy from the transmitter coil 9 to the implant's receiver coil. The stimulation of the retinal tissue causes a visual impression.

Figure 2:
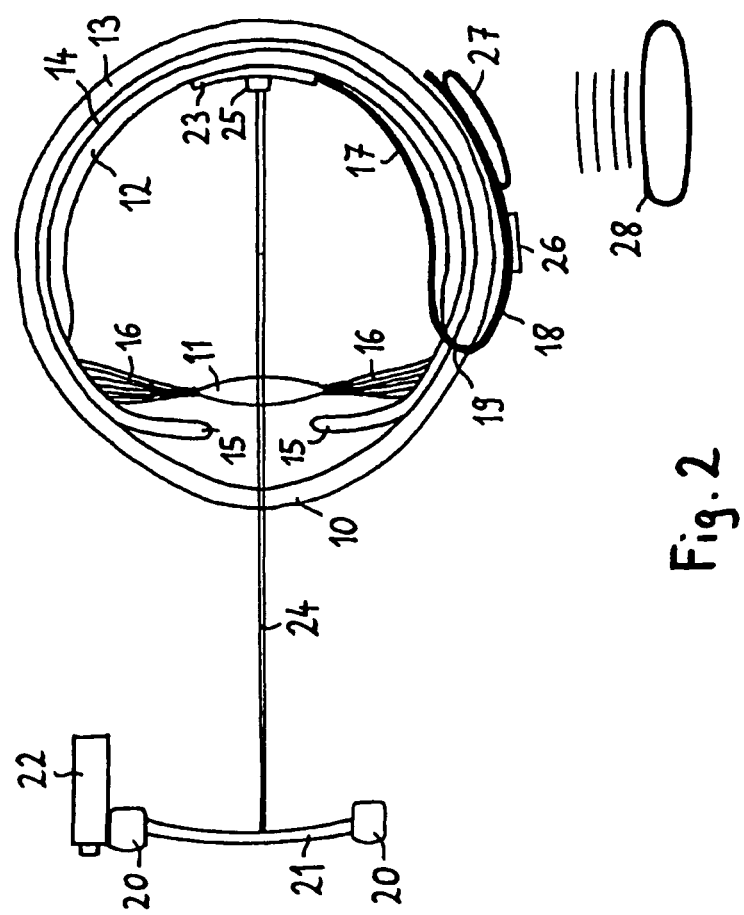
FIG. 2 shows a cross section of an eyeball comprising a retina implant.

FIG. 2 shows a cross section of a patient's eye comprising a retinal implant. External light passes the cornea 10 and the eye lens 11 and strikes the retina 12. The retina 12 covers a large part of the eyeball's interior. The eyeball's outer surface is formed by the sclera 13. Between the retina 12 and the sclera 13, a choroid membrane 14 is located. The iris 15 determines the amount of light that may enter into the interior of the eye. The eye lens 11 is fixed by the ciliary muscle 16.

The retina implant comprises an intraocular part 17 and an extraocular part 18. The intraocular part 17 is located in the interior of the eye, whereas the extraocular part 18 is fixed to the outer surface of the sclera 13. The intraocular part 17 and the extraocular part 18 are electrically connected by wire connections 19 that pass through the sclera 13 at a position right behind the ciliary muscle 16.

The patient wears an eyeglass frame 20 with glasses 21, with a small video camera 22 being integrated in the eyeglass frame 20. The video signals acquired by the video camera 22 are forwarded to the pocket computer 7 shown in FIG. 1. There, the video signals are converted into corresponding stimulation data for an array 23 of microcontacts located directly on the retina 12.

In the embodiment depicted in FIG. 2, a modulated infrared beam 24 is used for transmitting the stimulation data to the retina implant. The infrared beam 24 may for example be generated by an infrared transmitter LED located in the vicinity of the glasses 21. The modulated infrared beam 24 passes through the eye lens 11 and strikes an optical receiver element 25 (e.g. a photodiode) located on the intraocular part 17 of the retina implant. The stimulation data received by the optical receiver element 25 is forwarded via the wire connection 19 to a retina stimulation chip 26 located on the extraocular part 18 of the retina implant. Preferably, the retina stimulation chip 26 is implemented as a digital signal processing chip. The retina stimulation chip 26 is operative to convert the stimulation data into corresponding stimulation pulses for the array 23 of microcontacts. The stimulation pulses are supplied to the array 23 of microcontacts via the wire connection 19. The microcontacts are adapted for stimulating the ganglia of the retina 12.

The extraocular part 18 of the retina implant comprises a high frequency receiver coil 27 that is inductively coupled with a high frequency transmitter coil 28. Thus, the electrical power required for operation of the retina implant can be provided by the RF transmitter coil 28, which may e.g. be integrated in one of the temples of the eyeglass frame.

In case a patient intends to watch television via the video camera integrated in the visual interface, the image acquisition rate of the video camera may not match with the refresh rate of the television set. As a result of this mismatch, flickering of the TV image will occur, and therefore, watching TV will be difficult for the patient.

According to embodiments of the present invention, it is proposed to supply the TV signal or the signal of any other external signal source directly to the pocket computer, which is responsible for converting the signal of the respective external signal source into corresponding stimulation data for the patient's retina implant.

Figure 3:
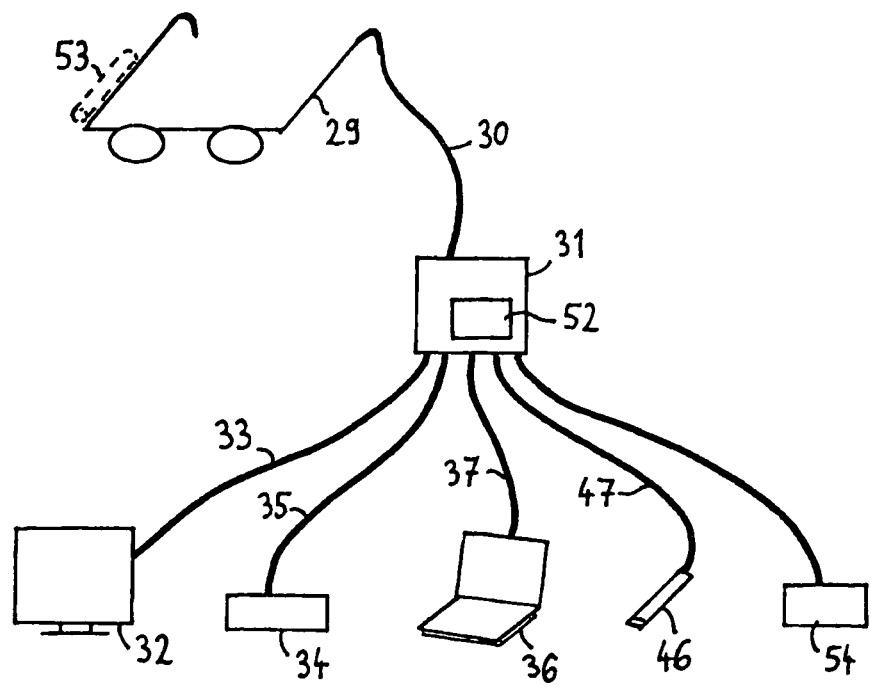
FIG. 3 shows a variety of external signal sources that may be connected to the visual prosthesis system.

FIG. 3 shows an embodiment of the present invention. A visual interface 29 is connected, via a wired or wireless connection 30, to a pocket computer 31. The pocket computer 31 may be connected with one or more different external signal sources. For example, the pocket computer 31 may be connected with a TV set 32 via a wired or wireless connection 33. Additionally or alternatively, the pocket computer 31 may be connected with a video device 34 via a wired or wireless connection 35. The video device 34 may for example be a satellite receiver, a DVB-T (Digital Video Broadcasting Terrestrial) receiver, or a DVD player. At least one of the connections 33, 35 may for example be realized as a cable connection, in particular as one of: a SCART cable, a HDMI (High Definition Multimedia Interface) cable, a VGA (Video Graphics Array) cable, an USB (Universal Serial Bus) cable, a coaxial cable, a two-wire cable, a twisted pair connection, a glass fiber, etc. At least one of the connections 33, 35 may e.g. be implemented as a wireless connection, in particular as one of: a WLAN (Wireless Local Area Network) connection, a Bluetooth connection, an UMTS (Universal Mobile Telecommunications System) connection, or any other kind of radio connection or wireless optical connection.

At the pocket computer 31, video signals supplied by the TV set 32 or the video device 34 are converted into corresponding stimulation data for the patient's retina implant. Via the connection 30, the stimulation data is forwarded to the visual interface 29, and from there, the stimulation data is transmitted to the retina implant. The stimulation data causes a visual impression that corresponds to the respective video signal.

Alternatively or additionally, a personal computer 36 or a laptop may be connected, via a wired or wireless connection 37, to the pocket computer 31. The personal computer 36 may be operative to provide a video data stream to the patient's pocket computer 31. Preferably, a common video standard like for example MPEG (Moving Picture Expert Group) or AVI (Audio Video Interleaved) may be employed. The video data stream may either be transmitted as a non-compressed or as a compressed data stream. At the pocket computer 31, the video data stream is converted into corresponding stimulation data for the visual interface 29. The stimulation data is transmitted to the visual interface 29 and to the retina implant.

The personal computer 36 may as well be used for displaying images, text files and internet sites to the patient. The respective data is supplied to the pocket computer 31, and the pocket computer 31 is adapted for converting the data into corresponding stimulation data for the retina implant. The display of text files, like e.g. emails, internet sites or documents of a word processing program is an important issue for the patient.

However, retinal implants that are currently in use comprise an array of 7×7 microcontacts. Though it is to be expected that the resolution provided by the retinal implant will become better and better during the following years, the display of text in a readable manner will remain a challenge during the next years.

According to an aspect of the present invention, it is proposed to provide a dedicated text display mode for displaying text on a retina implant in a way that the patient may easily read the displayed text.

In case of text being represented as a text file, e.g. as a sequence of codes like e.g. ASCII codes or in a similar representation, the characters identified by the character codes may successively be displayed to the patient. For display of the characters, the resolution provided by the array of microcontacts may be taken into account by defining character fonts that match with the resolution of the array of microcontacts. For example, in FIG. 4, it is shown how a character 38 of a text file is displayed to a patient on the retina implant. Each character is displayed in a way that an optimum legibility is accomplished. The microcontacts of the retina implant are stimulated according to a specific character font, and thus, optimum legibility is accomplished. Preferably, the font is chosen such that the entire array of microcontacts comprising M rows and N columns is utilized for displaying a character.

According to a preferred embodiment, the different characters of the text are displayed subsequently, whereby each character is displayed for a certain period of time, and then, a subsequent character of the text file is shown. The prosthesis system may e.g. comprise input means for selecting the speed of the display. Furthermore, the patient may select a most suitable font from a plurality of different fonts.

Further preferably, the text display mode may include a zoom functionality for varying the font size of the displayed characters.

Figure 5:
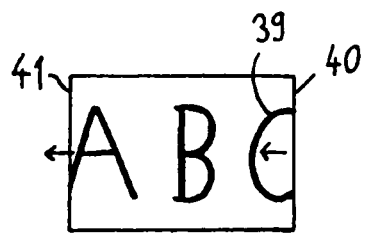
FIG. 5 shows how text may be scrolled across the display area.

Another possibility for displaying text data is to scroll the characters across the display area of the retina implant. This embodiment is illustrated in FIG. 5. A character 39 entering the display area at the right side 40 is scrolled across the display area from right to left and will disappear at the left side 41 of the display area. Thus, the text is displayed to the user as a ticker. The prosthesis system may comprise input means for controlling the progression speed of the text scrolled across the display. The patient may adapt the display speed to his or her reading preferences. In particular, the patient may speed up or slow down the text display. It may even be possible to move back by a certain number of characters, in order to repeat reading a certain passage of text. In a preferred embodiment, a remote control is used for adjusting the display speed.

Figure 6:
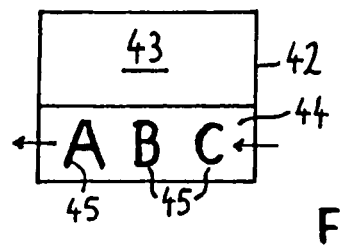
FIG. 6 illustrates how the display area of the retina implant may be split into different portions.

FIG. 6 shows another preferred display mode for displaying text data on the retina implant. The display area 42 is split into an upper part 43 and a lower part 44. In the lower part 44, characters 45 are scrolled across the display from right to left. In the upper part 43, images or video streams may be displayed. Preferably, in the upper part 43, a full view of a document currently read by the patient may be given. Alternatively, in the upper part 43, a video stream acquired by a video camera integrated in the visual interface may be displayed.

So far, techniques for displaying characters of a text file in a dedicated text display mode have been described. These techniques may be applied whenever text data comprising ASCII codes or a similar representation is to be displayed. However, text may also be present in bitmap data, for example in an image file or in a video stream.

To enable a blind or visually impaired person to read paper documents, a handheld scanner connected to the visual prosthesis system may be a helpful tool for reading paper documents. In FIG. 3, a handheld scanner 46 is shown. The handheld scanner 46 may be connected, via a wired or wireless connection 47, to the pocket computer 31. The handheld scanner 46, or any scanner attached to the personal computer 36, is adapted for generating a bitmap image of a paper document. The bitmap image generated by the scanner may be directly displayed to the patient's retina implant. Alternatively, character recognition techniques may be employed for converting the bitmap data provided by the scanner into a corresponding text file comprising a sequence of ASCII codes or a similar representation.

Figure 7A:
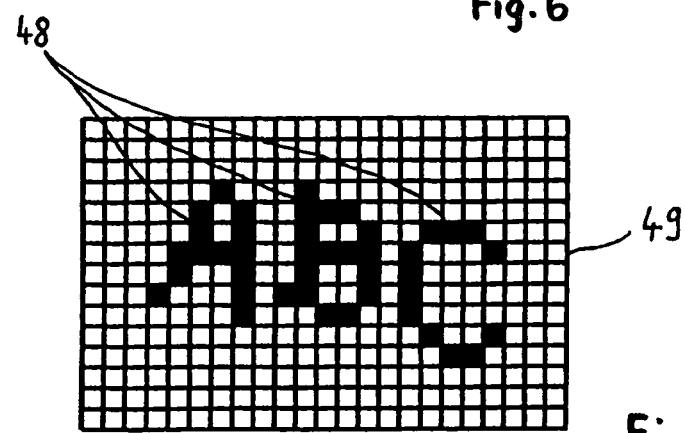
FIGS. 7A and 7B illustrates how characters in a bitmap file may be aligned with the rows and columns of the display area; and FIG. 8A
Figure 7B:
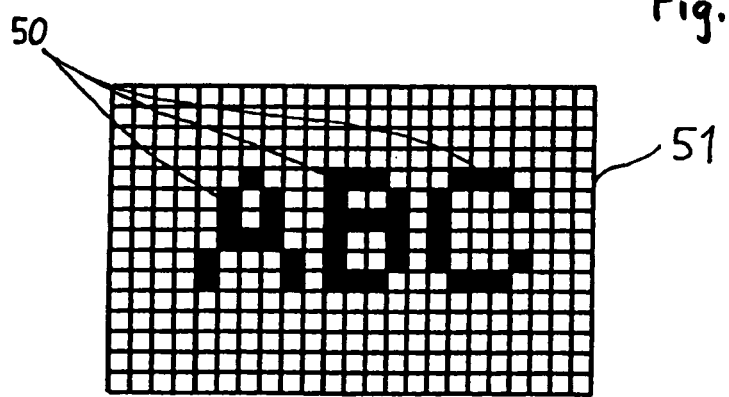

In FIGS. 7A and 7B, it is illustrated how the display of bitmap data containing text can be improved. In FIG. 7A, a bitmap of the characters 48 is displayed on a display area 49 of the retinal implant. The characters 48 are not aligned with the columns and rows of the array of microcontacts, and therefore, the characters 48 are hard to read. As shown in FIG. 7B, an improvement can be accomplished by aligning the characters 50 with the columns and rows of the implant's display area 51.

Figure 4:
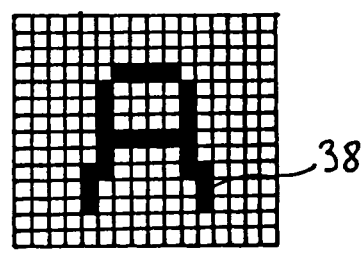
FIG. 4 shows a character that is displayed in a dedicated text display mode.

Alternatively, character recognition techniques may be employed for converting the bitmap data provided by an external signal source like e.g. a scanner into a corresponding text file comprising a sequence of ASCII codes or a similar representation. For example, the pocket computer 31 shown in FIG. 3 may comprise a character recognition unit 52 adapted for converting bitmap data into a text file. For example, the patient may use the handheld scanner 46 for scanning a paper document, with the character recognition unit 52 being responsible for converting the scanned bitmap data into text. The text may then be displayed on the retina implant using a dedicated text display mode as described above. For example, a character font may be used that is well-suited to the implant's resolution, as shown in FIG. 4. Furthermore, the text may be scrolled across the display from right to left, as shown in FIGS. 5 and 6.

The visual interface 29 shown in FIG. 3 may comprise an intrasystem video camera 53 integrated into the eyeglass frame. The video camera 53 acquires video data that corresponds to the presumable field of view of the patient. The acquired video data is forwarded to the pocket computer 31. In addition to the intrasystem video camera 53, one or more of the following external signal sources may be connected to the pocket computer 31: the TV set 32, the video device 34, the personal computer 36 or the handheld scanner 46 or any other external signal source 54.

In case an external signal source is connected to the pocket computer 31, the pocket computer 31 may either convert the video images provided by the intrasystem video camera 53 or the external signals provided by the respective external signal source into corresponding stimulation data for the retina implant. Hence, in case the visual interface 29 comprises a video camera 53, the patient may select between the image provided by the video camera and the image provided by a respective external signal source.

Alternatively, a dedicated visual interface 29 without any integrated video camera may be employed solely for watching TV, reading text files or surfing in the Internet. Therefore, in FIG. 3, the intrasystem camera 53 has been indicated with dashed lines.

In the context of the present application, the term "external signal source" shall comprise any network or device capable of providing an external signal like for example video data, image data or text data to the pocket computer 31. The term "external signal source" does not include the intrasystem video camera 53, which is to be seen as an intrasystem camera of the visual prosthesis system.

Figure 8A:
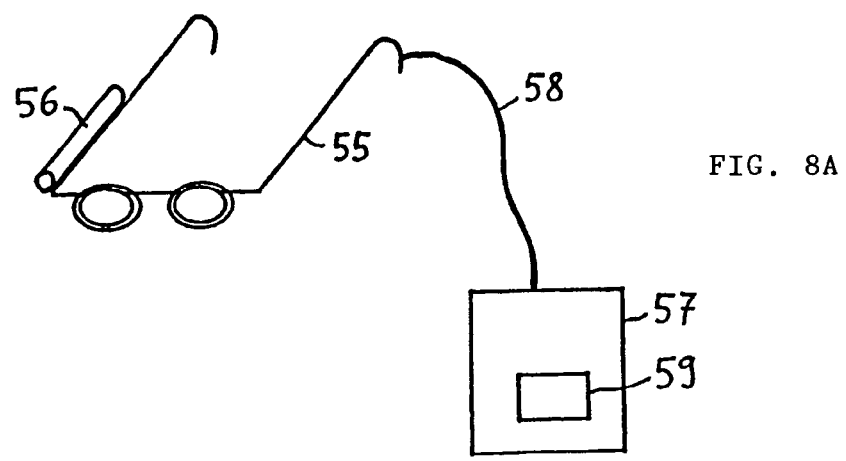
FIG. 8B shows how character recognition may be applied to a bitmap image acquired by the system's intrasystem video camera.
Figure 8B:
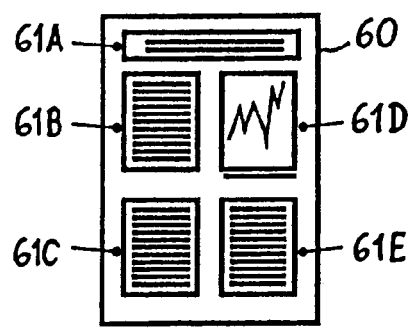

In FIG. 8A and FIG. 8B, another embodiment of the present invention is illustrated. The visual prosthesis system shown in FIG. 8 comprises a visual interface 55 with an intrasystem video camera 56 and a pocket computer 57 that is connected to the visual interface 55 via a wired or wireless connection 58. The pocket computer 57 comprises a character recognition unit 59 that is capable of converting bitmap images acquired by the intrasystem video camera 56 into a corresponding text file. The text file may then be displayed on the retina implant, whereby the above-described dedicated text display mode may be utilized.

For example, the camera 56 may acquire a snapshot of a paper document 60 comprising five areas of text 61A to 61E. The acquired image of the document 60 is displayed on the retina implant, and the patient may select one of the areas of text 61A to 61E. For this purpose, the prosthesis system may comprise suitable input means for selecting one of the areas of text. Once the selection has been made, the portion of the bitmap image that corresponds to the selected area is analyzed by the character recognition unit 59, and the bitmap data is converted into a stream of character codes. The sequence of characters may then be displayed to the patient using a dedicated text display mode. Preferably, the text is displayed in accordance with one of the methods illustrated in FIGS. 4 to 6.

According to a further embodiment, the patient may toggle between a standard representation of his surrounding and a dedicated text display mode. In case the patient switches to text display mode, an area of text located at the center of the patient's field of view may automatically be converted into a text file by the character recognition unit 59, and the obtained text file may be displayed using the dedicated text display mode.

The invention claimed is:

1. A visual prosthesis system comprising
  a retina implant at least partly located in the interior of a patient's eye, the retina implant comprising an array of micro-contacts adapted for contacting ganglia of the patient's retinal tissue,
  a data processing unit with an additional interface for receiving an external signal from an external signal source, the data processing unit being adapted for converting the external signal into corresponding stimulation data for the retina implant,
  a wireless transmission unit adapted for transmitting the stimulation data to the retina implant via wireless transmission,
  the retina implant being adapted for receiving the stimulation data and for stimulating the micro-contacts according to the stimulation data,
  wherein the data processing unit comprises a character recognition unit adapted for recognizing characters in a bitmap image provided by the external signal source, and for converting the bitmap image into text data.

2. The visual prosthesis system of claim 1, further comprising an intrasystem video camera adapted for acquiring a video signal that corresponds to the patient's field of view, wherein the data processing unit is adapted for receiving the video signal from the intrasystem video camera and for converting the video signal into corresponding stimulation data for the retina implant.

3. The visual prosthesis system of claim 2, further comprising input means for selecting either the video signal of the intrasystem video camera or the external signal of the external signal source to be displayed to the patient on the retina implant.

4. The visual prosthesis system of claim 1, wherein the external signal source is one of: a TV set, a video device, a personal computer, a laptop, a satellite receiver, a DVB receiver, a DVD player.

5. The visual prosthesis system of claim 1, wherein the connection between the data processing unit and the external signal source is a cable connection, in particular one of: a SCART cable, a High Definition Multimedia Interface cable, a Video Graphics Array cable, an Universal Serial Bus cable, a coaxial cable, a two-wire cable, a twisted pair connection, a glass fiber.

6. The visual prosthesis system of claim 1, wherein the connection between the data processing unit and the external signal source is a wireless connection, in particular one of: a Wireless Local Area Network connection, a Bluetooth connection, an Universal Mobile Telecommunications System connection, a radio connection, a wireless optical connection.

7. The visual prosthesis system of claim 1, wherein the external signal is one of a video signal, an image signal and text data.

8. The visual prosthesis system of claim 1, wherein the external signal source is a hand-held scanner adapted for providing a bitmap image to the data processing unit.

9. The visual prosthesis system of claim 1, wherein the data processing unit is adapted for converting the text data into corresponding stimulation data for the retina implant.

10. The visual prosthesis system of claim 9, wherein the text data is displayed in accordance with a dedicated text display mode.

11. A visual prosthesis system comprising
a retina implant at least partly located in the interior of a patient's eye, the retina implant comprising an array of micro-contacts adapted for contacting ganglia of the patient's retinal tissue,
an intrasystem video camera adapted for acquiring a video signal,
a data processing unit adapted for receiving the video signal from the intrasystem video camera and for converting the video signal into corresponding stimulation data for the retina implant,
a wireless transmission unit adapted for transmitting the stimulation data to the retina implant via wireless transmission,
the retina implant being adapted for receiving the stimulation data and for stimulating the micro-contacts according to the stimulation data,
wherein the data processing unit is adapted for determining if a received signal comprises text, and for converting the text into corresponding stimulation data for the retina implant according to a dedicated text display mode, wherein the stimulation data is adapted to provide for an optimized legibility of the text by the patient.

12. The visual prosthesis system of claim 11, wherein the data processing unit comprises an additional interface for receiving an external signal, the data processing unit being adapted for determining if the external signal comprises text, and for converting the text into corresponding stimulation data for the retina implant according to the dedicated text display mode.

13. The visual prosthesis system of claim 12, wherein the text is received via the additional interface as text data, the text data comprising a sequence of character codes.

14. The visual prosthesis system of claim 11, wherein the data processing unit comprises a character recognition unit adapted for recognizing characters in a bitmap image, and for converting the bitmap image into text data.

15. The visual prosthesis system of claim 14, wherein the bitmap image is acquired by the intrasystem video camera.

16. The visual prosthesis system of claim 14, wherein the bitmap image is received via an additional interface from an external signal source.

17. The visual prosthesis system of claim 14, further comprising input means for selecting a text portion of the bitmap image to be subjected to character recognition.

18. The visual prosthesis system of claim 11, further comprising at least one of the following features:
the data processing unit is adapted for displaying the characters of the text on the retina implant with a font that matches with the resolution provided by the retina implant;
the visual prosthesis system comprises input means for selecting, from a plurality of different fonts, a dedicated font that provides for an optimum legibility of the text;
substantially the full size of the retina implant's display area is utilized for displaying the text to the patient;
the visual prosthesis system comprises input means for varying the font size of the text;
the data processing unit is adapted for scrolling characters of the text across a display area of the retinal implant;
the data processing unit is adapted for displaying the text as a ticker;
the data processing unit is adapted for splitting up the display area of the retina implant into different portions, with at least one portion being employed for displaying the text as a ticker;
the data processing unit is adapted for displaying the characters of the text one after the other, each character being displayed for a predefined period of time before a subsequent character is displayed.

19. A method for displaying text data in a visual prosthesis system, the visual prosthesis system comprising a retina implant at least partly located in the interior of a patient's eye, the retina implant comprising an array of micro-contacts adapted for contacting ganglia of the patient's retinal tissue, and a data processing unit;
the method comprising:
acquiring a video signal by an intrasystem video camera or receiving an external signal from an external signal source,
determining whether the acquired video signal or the external signal from the external signal source comprises text,
converting the text into corresponding stimulation data for the retina implant according to a dedicated text display mode, wherein in the text display mode, the stimulation data is adapted to provide for an optimized legibility of the text by the patient,
transmitting the stimulation data to the retina implant via wireless transmission,
stimulating the micro-contacts according to the stimulation data.

20. The method of claim 19, further comprising
recognizing characters in a bitmap image, and
converting the bitmap image into text data.

* * * * *